(12) United States Patent
Sorensen

(10) Patent No.: US 7,235,065 B1
(45) Date of Patent: Jun. 26, 2007

(54) ADJUSTABLE HOLDER FOR AN EYEDROPPER

(76) Inventor: Peter H. Sorensen, 189-18 35th Ave., Flushing, NY (US) 11358

( * ) Notice: Subject to any disclaimer, the term of this patent is extended or adjusted under 35 U.S.C. 154(b) by 341 days.

(21) Appl. No.: 10/422,086

(22) Filed: Apr. 24, 2003

(51) Int. Cl.
*A61M 35/00* (2006.01)

(52) U.S. Cl. .................. 604/302; 604/294; 604/295; 604/300

(58) Field of Classification Search ......... 604/294–302
See application file for complete search history.

(56) References Cited

U.S. PATENT DOCUMENTS

| | | | |
|---|---|---|---|
| 2,722,216 A * | 11/1955 | Robbins ................. | 604/302 |
| 3,058,466 A | 10/1962 | Routsong | |
| 3,872,866 A | 3/1975 | Lelicoff | |
| 3,934,590 A | 1/1976 | Campagna et al. | |
| D249,709 S | 9/1978 | Trovinger | |
| 4,134,403 A | 1/1979 | Johnsen et al. | |
| 4,685,906 A | 8/1987 | Murphy | |
| 4,792,334 A * | 12/1988 | Py ......................... | 604/301 |
| 4,960,407 A | 10/1990 | Cope | |
| 4,973,322 A * | 11/1990 | Jewart ..................... | 604/300 |
| 5,429,621 A | 7/1995 | Stahl | |
| 6,159,188 A * | 12/2000 | Laibovitz et al. ......... | 604/294 |
| D463,550 S | 9/2002 | Sherman | |
| 2003/0032930 A1* | 2/2003 | Branch .................... | 604/298 |

* cited by examiner

*Primary Examiner*—Tatyana Zalukaeva
*Assistant Examiner*—Melanie J. Hand
(74) *Attorney, Agent, or Firm*—Collard & Roe, P.C.

(57) ABSTRACT

The invention relates to a holder for an eyedropper comprising a base having a top surface, a bottom surface, and side surfaces wherein the base has at least one interface for receiving the eyedropper. There is also a support coupled to the base and extending from the bottom surface of this base. Extending out from this support is a first leg and a second leg. These legs branch apart to form a slot or support groove therebetween. There is also a track formed on the bottom surface of the base wherein the support is adjustably coupled to the track so that the support can slide along the track. At least one band can be coupled to the base. The band is allows an eyedropper to attach to the holder.

10 Claims, 2 Drawing Sheets

ADJUSTABLE HOLDER FOR AN EYEDROPPER

BACKGROUND

The invention relates to an adjustable holder for eyedroppers. Eyedrop dispensing devices are known in the art. In particular, eyedrop dispensers that have a base are known in the art. For example U.S. Pat. Nos. 6,508,793, 4,960,407, 4,685,906, 5,665,079, 4,134,403, 3,872,866, 3,934,590, 4,792,334, 4,973,322, and 3,058,466. Some of the problems of the above references are the complexity of design, and the lack of adjustability or accuracy in the positioning of the eyedropper to deliver eyedrops.

SUMMARY

The invention relates to a holder for an eyedropper comprising a base having a top surface, a bottom surface, and side surfaces wherein the base has at least one interface for receiving the eyedropper. There is also a support coupled to the base and extending from the bottom surface of this base. Extending out from this support is a first leg and a second leg. These legs branch apart to form a slot or support groove therebetween. There is also a track formed adjacent to the bottom surface of the base wherein the support is adjustably coupled to the track so that the support can slide along the track.

To attach an eyedropper to the holder, there is at least one band. The band can be elastic and attaches the eyedropper to the base in a region of the interface. This interface can be shaped in a form of a groove or wedge disposed on the front surface of the base. Extending out of a back side or surface of the base is at least one flange or leg, but preferably two legs forming a slot or recess.

Once the eyedropper is coupled to the base via the band, it can be adjusted in relation to the support because the support can selectively slide along the track. For example, this track contains a plurality of notches and the support contains a plurality of notches to selectively secure the support along the track in the base and to selectively keep the support from moving along the track.

This holder is designed so that the central support groove on the support extends transverse to a direction of adjustment of the support in relation to the base, so that once the holder is placed on a person's nose, the support can still be adjusted along the track.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION

Figures 1, 2:
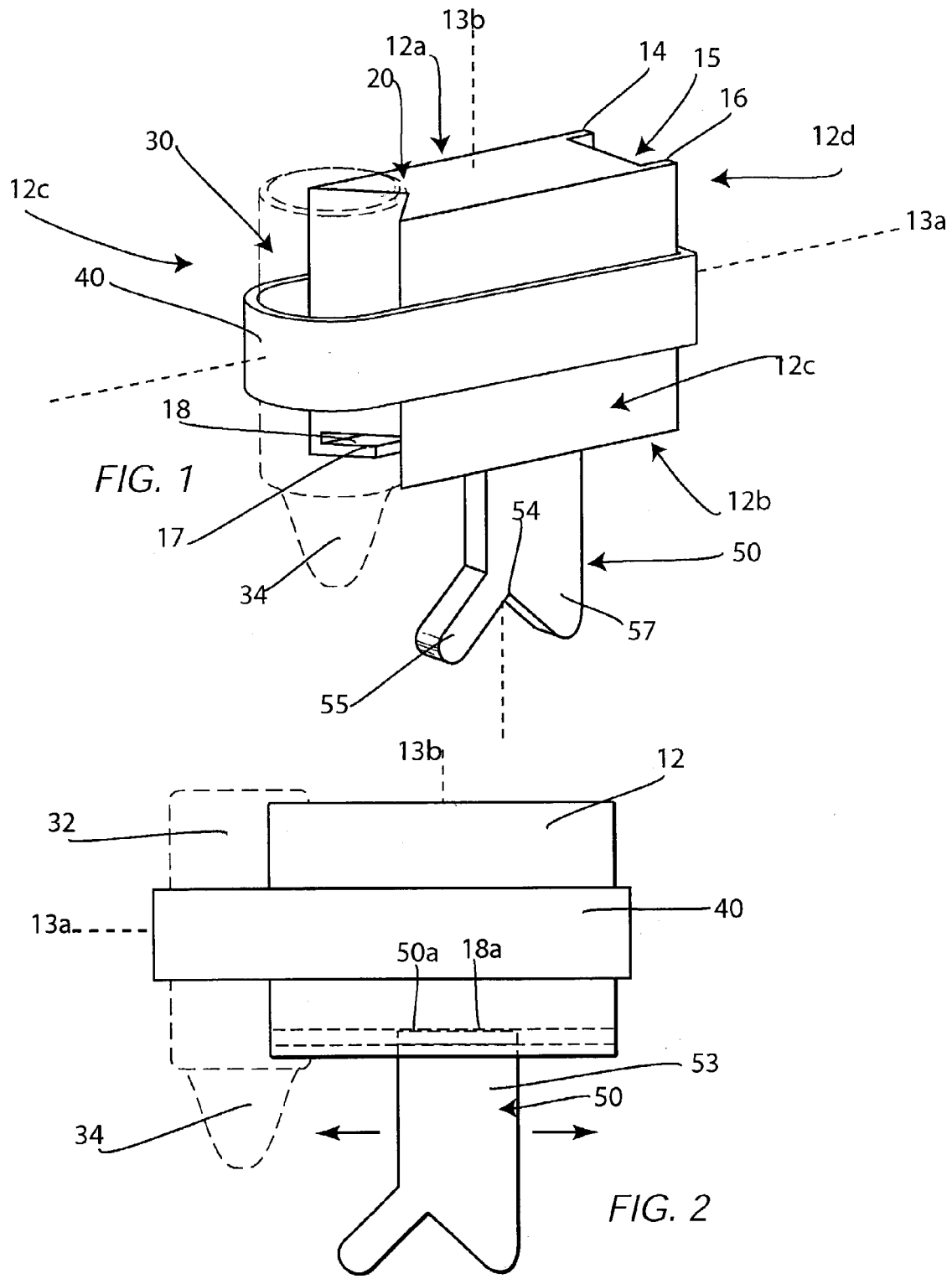
FIG. 1 is a perspective view of the adjustable eyedropper holder showing the eyedropper in dashed lines.
FIG. 2 is a side view of the adjustable eyedropper holder showing the eyedropper in dashed lines.

Referring to the drawings, FIG. 1 shows a perspective view of a holder 10 for an eyedropper comprising a base 12, a band or holder 40 and a support or base leg 50. Base 12 is substantially rectangular shaped and has six sides, and when positioned upright, these six sides form a top side 12a, a bottom side 12b, a front side 12c, a back side 12d and two lateral sides 12e and 12f (FIG. 3) extending along a longitudinal axis 13a. When holder 10 is positioned upright, longitudinal axis 13a is substantially horizontal while latitudinal axis 13b is substantially vertical. Base 12 has two parallel spaced back flanges or attachment sections 14 and 16 which extend out from back side 12d and are spaced apart to form a slot or recess 15.

Base 12 also has a track or adjustment section 18 which can be in the form of a groove wherein track 18 is disposed adjacent to bottom side 12b. Track 18 is formed as a recess in base 12 which is substantially covered on bottom side 12b by flanges or locking sections 17 and 19 (see FIG. 3). As shown in FIG. 2, track 18 has a plurality of notches or adjustment elements 18a which allow an element such as support 50 to be selectively slided along track 18. There can also be a smooth shaped track (not shown) to allow support to freely slide along track 18.

Front side 12c of base 12 has a connection interface or holding section 20 which can be formed as a wedge shaped groove. Interface 20 has two lateral sides 22 and 24 extending out in a V-shape for supporting an eyedropper 30 against lateral movement when eyedropper 30 is coupled to base 20 via band 40. Eyedropper 30 has a bottle section 32, and a conical delivery section, or nozzle 34 wherein when eyedropper 30 is coupled to base 12, bottle section 32 is in contact with band 40 and interface 20 while delivery section or nozzle 34 extends beyond or below base 12.

Figure 3:
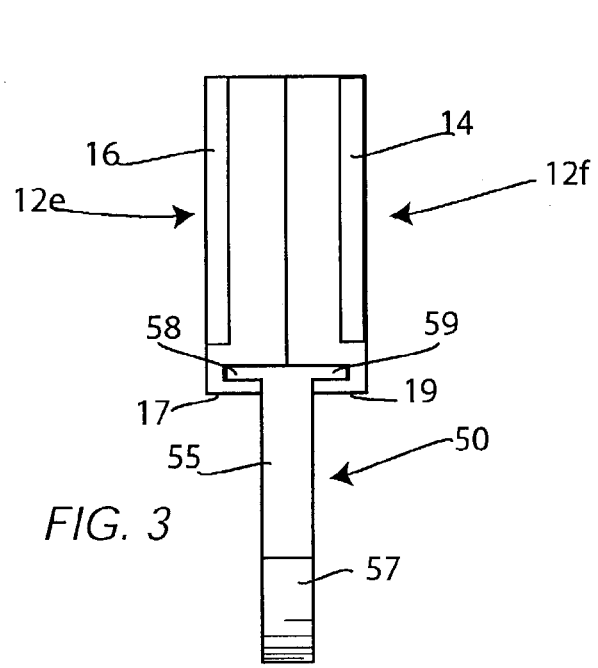
FIG. 3 is a back view of the adjustable eyedropper holder.

Support 50 is for supporting base 12 above a user's nose when support 50 is placed on a user's nose. Support 50 has a base section 53 and two legs 55 and 57 which branch out from base section 53 opposite a region where support 50 attaches to base 12. First leg 55 is thinner than second leg 57 wherein both legs 55 and 57 branch out to form a slot 54 which can be in the form of a wedge shaped groove for providing lateral support for support 50 on a user's nose. Slot or Groove 54 extends along support 50 transverse to longitudinal axis 13a and also transverse to the direction of adjustment of support 50 in base 12. As shown in FIG. 3, support 50 also contains attachment elements or flanges 58 and 59 extending out from support 50 opposite legs 55 and 57. Flanges 58 and 59 slide in track 18 wherein as shown in FIG. 2, a top or attachment surface of support 50 contains notches or adjustment elements 50a for allowing support 50 to be selectively engaged with notches 18a in base 12 while still being selectively slidable along track 18.

Figure 4:
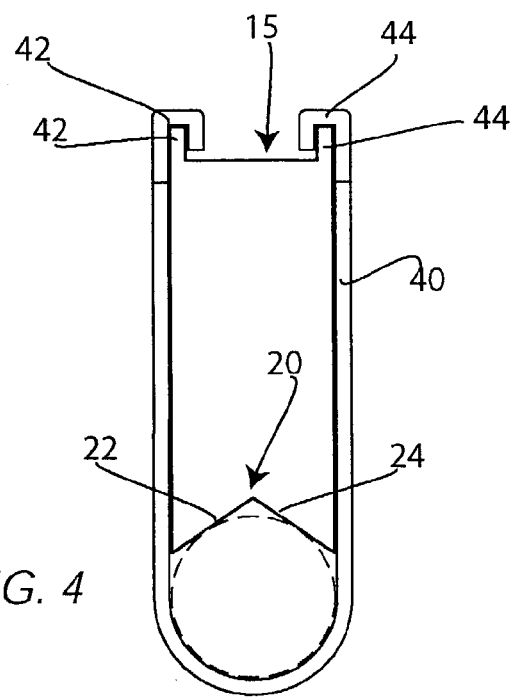
FIG. 4 is a top view of the adjustable eyedropper holder.

FIG. 4 shows a top view of holder 10 which shows how band 40 connects to base 12. For example, band 40 has attachment sections, or attachment elements 42 and 44 which attach to flanges or legs 14 and 16 so that band 40 can be secured to base 12.

Figure 5:
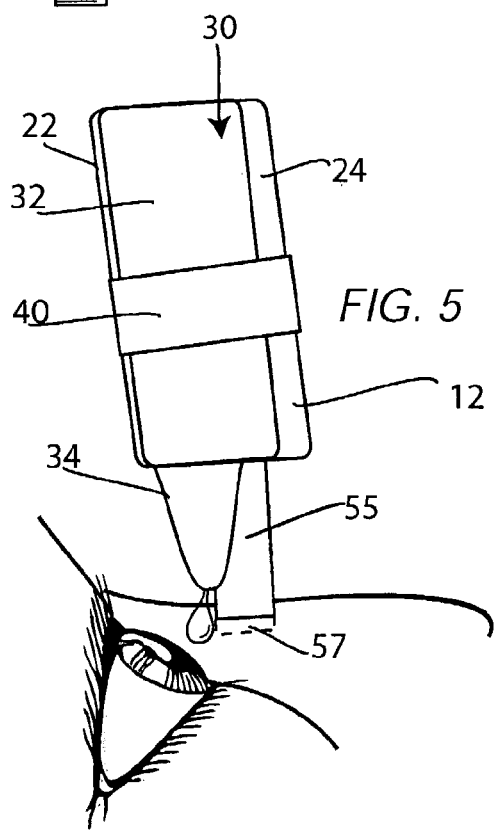
FIG. 5 is a perspective view of the adjustable eyedropper holder in use.

FIG. 5 shows the front side 12a of holder 10 wherein holder 10 is in use. Thus, to use holder 10, a user tilts his or her head back and places support 50 on his or her nose. First leg 55 extends over one side of the user's nose while second leg 57 extends over the other side so that groove 54 is situated on a top section of the user's nose. In this position, support 50 and base 12 are laterally supported in relation to a user's nose for accurate and easy placement of eye drops in a user's eyes. Track 18 allows support 50 to be adjusted along base 12 so that a user can adjust the position of nozzle 34 on eyedropper 30 in relation to his eyes for an accurate insertion of eye drops.

One of the benefits of this design, is that once an eye drop is administered to a user's eye, the eyedropper holder can be rotated approximately 180 degrees so that first leg 55 and second leg 57 extend over opposite sides of the nose and nozzle 34 is positioned over the user's other eye. In this position, the user can then administer the eye drops to the second eye.

Accordingly, while at least one embodiment of the present invention has been shown and described, it is to be understood that many changes and modifications may be made thereunto without departing from the spirit and scope of the invention as defined in the appended claims.

What is claimed is:

1. A holder for an eyedropper comprising: a) an elongated base having a top surface, a bottom surface and side surfaces wherein said base has at least one interface for receiving the eyedropper and wherein said interface is disposed on a side surface of said base; b) a support adjustably coupled to said base and extending from said bottom surface of said base; c) a first leg extending from said support; d) a second leg extending from said support, wherein said first leg and said second leg branch apart to forming a slot therebetween; e) a track, formed on said bottom surface of said base, wherein said support is adjustably coupled to said track, and said support is configured to slide along said track in a manner laterally from said nose such that an eyedropper is adjusted laterally in position in relation to a person's nose; and f) at least one elastic band for coupling the eyedropper to said base in a region of said interface.

2. The holder as in claim 1, wherein said interface is shaped in a form of a groove.

3. The holder as in claim 2, wherein said base further comprises at least one leg extending down a back side surface of said base, opposite said front side surface.

4. The holder as in claim 3, further comprising at least two clips wherein at least a first clip is coupled to one end of said band and also to said at least one leg and at least a second clip is coupled to an opposite end of said band and also to at least a second of said plurality of legs wherein said band is coupled to said base and extends around said base in a region of said interface.

5. The holder as in claim 1, wherein said track contains a plurality of notches to selectively secure said support along said base and to keep said support from moving along said track.

6. The holder as in claim 1, wherein said central groove on said support extends transverse to a direction of adjustment of said support and wherein said slot is sized to fit snugly over a user's nose.

7. The holder as in claim 5, wherein said support further comprises at least one flange coupled to said support, opposite said first leg and said second leg, wherein said at least one flange is for securing said support inside of said track.

8. The holder as in claim 5, wherein said support further comprises a plurality of notches to selectively secure said support to said notches on said base in said track.

9. A holder for an eyedropper comprising: a) an elongated base having a top surface, a bottom surface and side surfaces wherein said base has at least one interface for receiving the eyedropper and wherein said interface is disposed on a side surface of said base and being shaped as a wedge shaped groove; b) a support adjustably coupled to said base and extending from said bottom surface of said base; c) a first leg extending from said support; d) a second leg extending from said support; wherein said first leg and said second leg branch apart to forming a slot therebetween; e) a track formed on said bottom surface of said base wherein said support is adjustably coupled to said track so that said support is configured to slide along said track, wherein said track includes a plurality of notches disposed in the track to allow for the selective adjustment of said track; and f) at least one elastic band for coupling the eyedropper to said base in a region of said interface.

10. A holder for an eyedropper comprising: a) an elongated base having a top surface, a bottom surface and side surfaces wherein said base has at least one interface in the form of a groove for receiving the eyedropper and wherein said interface is disposed on a side surface of said base; b) a support adjustably coupled to said base and extending from said bottom surface of said base; c) a first leg extending from said support; d) a second leg extending from said support, wherein said first leg and said second leg branch apart to form a slot therebetween; e) a track, formed on said bottom surface of said base wherein said support is adjustably coupled to said track so that said support is configured to slide along said track; and f) at least one elastic band for coupling the eyedropper to said base in a region of said interface.

* * * * *